US012558339B2

(12) United States Patent
Oh

(10) Patent No.: US 12,558,339 B2
(45) Date of Patent: Feb. 24, 2026

(54) COMPOSITION COMPRISING (7S)-(+)-CYCLOPENTYL CARBARMIC ACID, 8,8-DIMETHYL-2-OXO-6,7-DIHYDRO-2H,8H-PYRANO[3,2-G]CHROMEN-7-YL-ESTER AS ACTIVE INGREDIENT FOR PREVENTION, ALLEVIATION, OR TREATMENT OF EYE DISEASE

(71) Applicants: INSPHARMTECH INC., Chuncheon-si Gangwon-do (KR); AREZ CO., LTD., Daejeon (KR)

(72) Inventor: Sang Taek Oh, Seoul (KR)

(73) Assignees: INSPHARMTECH INC., Chuncheon-si (KR); AREZ CO., LTD., Daejeon (KR)

( * ) Notice: Subject to any disclaimer, the term of this patent is extended or adjusted under 35 U.S.C. 154(b) by 404 days.

(21) Appl. No.: 18/272,465

(22) PCT Filed: Jan. 5, 2022

(86) PCT No.: PCT/KR2022/000112
§ 371 (c)(1),
(2) Date: Jul. 14, 2023

(87) PCT Pub. No.: WO2022/154356
PCT Pub. Date: Jul. 21, 2022

(65) Prior Publication Data
US 2024/0066000 A1 Feb. 29, 2024

(30) Foreign Application Priority Data
Jan. 14, 2021 (KR) ........................ 10-2021-0005273

(51) Int. Cl.
| A61K 31/27 | (2006.01) |
| A61K 9/00 | (2006.01) |
| A61K 31/366 | (2006.01) |
| A61P 27/02 | (2006.01) |

(52) U.S. Cl.
CPC ........... *A61K 31/27* (2013.01); *A61K 9/0048* (2013.01); *A61K 31/366* (2013.01); *A61P 27/02* (2018.01)

(58) Field of Classification Search
None
See application file for complete search history.

(56) References Cited

FOREIGN PATENT DOCUMENTS

| JP | 2012-525415 A | 10/2012 |
| KR | 10-1674145 B1 | 11/2016 |
| KR | 10-2338093 B1 | 12/2021 |
| WO | 2010/127029 A1 | 11/2010 |

OTHER PUBLICATIONS

Joong Gyu Ha et al., "Characterization of CGK012 in rat plasma by high performance liquid chromatography and mass spectrometry (HPLC-MS/MS): Application to a pharmacokinetic study", Journal of Pharmaceutical and Biomedical Analysis, Jul. 6, 2020, vol. 189, No. 113458, pp. 1-4 (4 pages).
Ying Yang et al., "Decursin inhibited proliferation and angiogenesis of endothelial cells to suppress diabetic retinopathy via VEGFR2", Molecular and Cellular Endocrinology, 2013, pp. 46-52, vol. 378.
Jeong Hun Kim et al., "Decursin inhibits retinal neovascularization via suppression of VEGFR-2 activation", Molecular Vision, 2009, pp. 1868-1875, vol. 15.
Jin Hyoung Kim et al., "Decursin inhibits VEGF-mediated inner blood-retinal barrier breakdown by suppression of VEGFR-2 activation", Journal of Cerebral Blood Flow & Metabolism, 2009, pp. 1559-1567, vol. 29.
International Search Report of PCT/KR2022/000112 dated Apr. 12, 2022 [PCT/ISA/210].

*Primary Examiner* — Samantha L Shterengarts
(74) *Attorney, Agent, or Firm* — Sughrue Mion, PLLC

(57) ABSTRACT

The present disclosure relates to a composition for preventing, alleviating or treating an eye disease, which contains (7S)-(+)-cyclopentylcarbarmic acid, 8,8-dimethyl-2-oxo-6,7-dihydro-2H,8H-pyrano[3,2-g]chromen-7-yl-ester as an active ingredient. The (7S)-(+)-cyclopentylcarbarmic acid, 8,8-dimethyl-2-oxo-6,7-dihydro-2H,8H-pyrano[3,2-g] chromen-7-yl-ester of the present disclosure exhibits the effect of remarkably reducing intraocular vascular leakage and, as such, can be advantageously used in a composition for preventing, alleviating or treating an eye disease.

9 Claims, 10 Drawing Sheets

1

COMPOSITION COMPRISING (7S)-(+)-CYCLOPENTYL CARBARMIC ACID, 8,8-DIMETHYL-2-OXO-6,7-DIHYDRO-2H,8H-PYRANO[3,2-G]CHROMEN-7-YL-ESTER AS ACTIVE INGREDIENT FOR PREVENTION, ALLEVIATION, OR TREATMENT OF EYE DISEASE

CROSS REFERENCE TO RELATED APPLICATIONS

This application is a National Stage of International Application No. PCT/KR2022/000112 filed on Jan. 5, 2022, claiming priority based on Korean Patent Application No. 10-2021-0005273 filed on Jan. 14, 2021.

TECHNICAL FIELD

The present disclosure relates to a composition for preventing, alleviating or treating an eye disease, which contains (7S)-(+)-cyclopentylcarbarmic acid, 8,8-dimethyl-2-oxo-6,7-dihydro-2H,8H-pyrano[3,2-g]chromen-7-yl-ester as an active ingredient.

BACKGROUND ART

Edema refers to excessive accumulation of body fluid such as plasma, interstitial fluid and transcellular between cells outside blood vessels due to leakage of the body fluid out of the blood vessels (i.e., vascular leakage).

Vascular leakage in the eye occurs for a variety of reasons. For example, continuously increased blood pressure in a hypertensive patient causes destruction of the blood-retinal barrier, and vascular leakage caused by the damage of the blood-retinal barrier results in retinal edema. The macular is sometimes damaged by macula tumentia following the removal of the eye lens for treatment of cataract.

Retinal edema refers to abnormal accumulation of fluid within the retina itself, whereas retinal detachment (peel) is characterized by abnormal accumulation of fluid in the subretinal space causing detachment of the retina from the underlying retinal pigment epithelium. The retinal detachment (peel) or edema in the center of the retina (macula) causes marked loss of vison and, eventually, leads to irreversible blindness (Yanoff and Duker, Ophthalmology, Mosby, Philadelphia, (1999); Wilkinson et al., Michel's Retinal Detachment, 2nd ed., Mosby, St. Louis, (1997)).

In diabetic retinopathy or wet (exudative) macular degeneration, visual impairment occurs as blood or exudate leaked from weak microvessels are accumulated. Until now, laser treatment has been known to be the most effective method effect method to prevent vascular leakage.

The existing methods for treating intraocular diseases include invasive surgery, local laser therapy, intravitreal drug administration, etc. It is known that commercially available drugs that are locally administered directly into the vitreous cavity require repetitive administration every 4-6 weeks, and the direct administration into the vitreous cavity causes inconvenience of medication, pain and side effects.

The matters described above as the background art are only for improving the understanding of the background of the present disclosure, and should not be taken as an admission that they correspond to the prior art already known to those having ordinary knowledge in the art.

The inventors of the present disclosure have researched to develop a drug which reduces the inconvenience of medication, can be administered for a long period of time and exhibits excellent therapeutic effect for eye diseases caused by intraocular vascular leakage. As a result, they have identified that (7S)-(+)-cyclopentylcarbarmic acid, 8,8-dimethyl-2-oxo-6,7-dihydro-2H,8H-pyrano[3,2-g]chromen-7-yl-ester can exhibit superior therapeutic effect in an intraocular vascular leakage-induced animal model by effectively inhibiting vascular leakage in the eye, and have completed the present disclosure.

DISCLOSURE

Technical Problem

The present disclosure is directed to providing a composition for preventing, alleviating or treating an eye disease.

Technical Solution

The present disclosure provides a pharmaceutical composition for preventing or treating an eye disease, which contains (7S)-(+)-cyclopentylcarbarmic acid, 8,8-dimethyl-2-oxo-6,7-dihydro-2H,8H-pyrano[3,2-g]chromen-7-yl-ester as an active ingredient.

In an exemplary embodiment of the present disclosure, the eye disease may be one or more disease selected from ocular neovascularization, macular degeneration, maculopathy, macular edema, retinal degeneration, retinal edema, retinopathy, macula tumentia and glaucoma.

In an exemplary embodiment of the present disclosure, the pharmaceutical composition may be a composition for topical administration to the eye.

In an exemplary embodiment of the present disclosure, the composition for topical administration to the eye may be formulated as an eye drop, an ointment or an ophthalmic injection.

In an exemplary embodiment of the present disclosure, the pharmaceutical composition may inhibit intraocular vascular leakage.

The present disclosure also provides a health functional food for preventing or alleviating an eye disease, which contains (7S)-(+)-cyclopentylcarbarmic acid, 8,8-dimethyl-2-oxo-6,7-dihydro-2H,8H-pyrano[3,2-g]chromen-7-yl-ester as an active ingredient.

Advantageous Effects

Since (7S)-(+)-cyclopentylcarbarmic acid, 8,8-dimethyl-2-oxo-6,7-dihydro-2H,8H-pyrano[3,2-g]chromen-7-yl-ester of the present disclosure exhibits the effect of remarkably reducing intraocular vascular leakage, it can be usefully used for a composition for preventing, alleviating or treating an eye disease.

BEST MODE

Figure 1A:
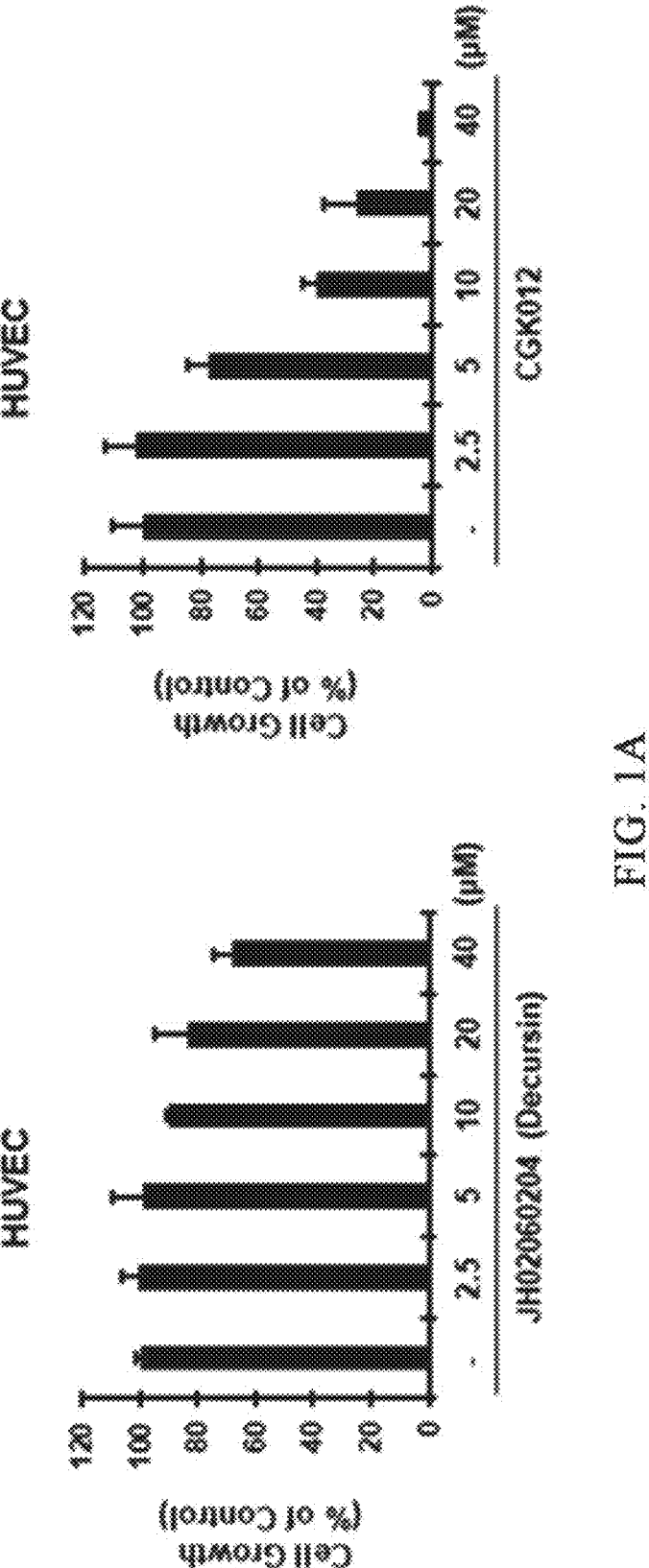
FIGS. 1A and 1B show a result of investigating the effect of a compound of an example (CGK012) and a compound of a comparative example (decursin) on the cell viability of human endothelial cells (HUVECs) (FIG. 1A) and the level of vascular endothelial growth factor (VEGF) in human retinal pigment epithelial cells (ARPE-19 cells) (FIG. 1B).

Hereinafter, the present disclosure is described in detail.

The inventors of the present disclosure have researched to develop a drug which reduces the inconvenience of medication, can be administered for a long period of time and exhibits excellent therapeutic effect for eye diseases caused by intraocular vascular leakage. As a result, they have identified that (7S)-(+)-cyclopentylcarbarmic acid, 8,8-dimethyl-2-oxo-6,7-dihydro-2H,8H-pyrano[3,2-g]chromen-7-yl-ester can exhibit superior therapeutic effect in an intraocular vascular leakage-induced animal model by effectively inhibiting vascular leakage in the eye, and have completed the present disclosure.

The present disclosure relates to a composition for preventing, alleviating or treating an eye disease, which contains (7S)-(+)-cyclopentylcarbarmic acid, 8,8-dimethyl-2-oxo-6,7-dihydro-2H,8H-pyrano[3,2-g]chromen-7-yl-ester as an active ingredient.

In the present disclosure, the term "vascular leakage" refers to leakage of body fluid or plasma components due to damage to the integrity of blood vessels. The vascular leakage in the eye ball is a major pathological condition of various eye diseases.

In the present disclosure, the term "intraocular vascular leakage" refers to vascular leakage in various tissues constituting the eye (choroid, retina, macula, etc.) and may specifically vascular leakage in the retina.

In the present disclosure, the prevention, alleviation or treatment of the eye disease may be achieved by inhibiting intraocular vascular leakage.

Specifically, the present disclosure provides a pharmaceutical composition for preventing or treating an eye disease, which contains (7S)-(+)-cyclopentylcarbarmic acid, 8,8-dimethyl-2-oxo-6,7-dihydro-2H,8H-pyrano[3,2-g]chromen-7-yl-ester as an active ingredient.

The present disclosure also provides a method for preventing, alleviating or treating an eye disease, which includes a step of administering (7S)-(+)-cyclopentylcarbarmic acid, 8,8-dimethyl-2-oxo-6,7-dihydro-2H,8H-pyrano[3,2-g]chromen-7-yl-ester or a pharmaceutically acceptable salt thereof to a subject in need thereof.

The present disclosure also provides a use of (7S)-(+)-cyclopentylcarbarmic acid, 8,8-dimethyl-2-oxo-6,7-dihydro-2H,8H-pyrano[3,2-g]chromen-7-yl-ester or a pharmaceutically acceptable salt thereof in therapy.

In the present disclosure, the use in therapy may be a use for treating an eye disease.

As used herein, the "subject" refers to a mammal which is a subject of prevention, alleviation, treatment, observation or experimentation. Specifically, it may be a human or a mammal in need of prevention, alleviation and/or treatment of an eye disease.

The compound of the present disclosure may be prepared into a pharmaceutically acceptable salt according to a conventional method in the art. In the present disclosure, the term "pharmaceutically acceptable" means that it is physiologically acceptable and does not usually cause allergic reactions such as gastrointestinal disorders, dizziness, etc. or similar reactions when administered to human. As the pharmaceutically acceptable salt, an acid addition salt formed from a pharmaceutically acceptable free acid is useful. The acid addition salt can be prepared by a conventional method, for example, by dissolving the compound in an excess aqueous solution of an acid and precipitating the formed salt in a water-miscible organic solvent, e.g., methanol, ethanol, acetone or acetonitrile. Alternatively, after heating an equimolar amount of the compound and an acid or an alcohol in water (e.g., glycol monomethyl ether), the mixture may be evaporated to dryness, or the precipitated salt may be suction-filtered.

The pharmaceutically acceptable salt includes an acid addition salt with an inorganic acid or an organic acid. As the acid addition salt, an acid addition salt formed from a pharmaceutically acceptable free acid is useful. The free acid may be an inorganic acid or an organic acid. As an inorganic acid, hydrochloric acid, hydrobromic acid, sulfuric acid, phosphoric acid, nitric acid, hydrioiodic acid, etc. may be used. As an organic acid, citric acid, acetic acid, lactic acid, tartaric acid, fumaric acid, mandelic acid, formic acid, propionic acid, oxalic acid, trifluoroacetic acid, methanesulfonic acid, benzenesulfonic acid, maleic acid, benzoic acid, gluconic acid, glycolic acid, succinic acid, 4-morpholinoethanesulfonic acid, camphorsulfonic acid, 4-nitrobenzenesulfonic acid, hydroxy-O-sulfonic acid, 4-toluenesulfonic acid, galacturonic acid, embolic acid, glutamic acid, glutaric acid, glucuronic acid, aspartic acid, ascorbic acid, carbonic acid, vanillic acid, etc. may be used. In addition, a base may be used to prepare the compound of the present disclosure into a pharmaceutically acceptable metal salt. An alkali metal or alkaline earth metal salt is obtained, for example, by dissolving the compound in an excess amount of an alkali metal hydroxide or alkaline earth metal hydroxide solution, filtering the undissolved compound salt, and then evaporating and drying the filtrate. As the metal salt, a sodium, potassium or calcium salt is particularly suitable for pharmaceutical purposes, and a corresponding silver salt may be obtained by reacting the alkali metal or alkaline earth metal salt with a suitable silver salt (e.g., silver nitrate).

In the present specification, "containing as an active ingredient" means that the compound of the present disclosure is contained in an amount sufficient to achieve the efficacy or activity of preventing, alleviating or treating an eye disease.

In the present specification, the term "prevention" means any action of suppressing or delaying the onset of an eye disease.

In the present specification, the term "improvement" means any action of at least lowering the parameters related with the condition to be treated, e.g., the severity of symptoms, by administering the pharmaceutical composition of the present disclosure.

In the present specification, the term "treatment" means any action of reversing, alleviating, inhibiting the progression of or preventing the symptoms of an eye disease, unless stated otherwise.

In an example of the present disclosure, it was confirmed that (7S)-(+)-cyclopentylcarbarmic acid, 8,8-dimethyl-2-oxo-6,7-dihydro-2H,8H-pyrano[3,2-g]chromen-7-yl-ester, which is a compound of the present disclosure, exhibits therapeutic effect for an eye disease by effectively inhibiting vascular leakage in an in-vivo choroidal neovascularization (CNV) animal model when dropped onto the eye. In addition, it was confirmed that it is distributed in the target tissue (eye) and exhibits therapeutic effect even when it was administered through different routes (intravitreal direct administration, oral administration, intraperitoneal injection, etc.).

Accordingly, the pharmaceutical composition of the present disclosure is effective for preventing or treating various eye diseases. The disease to which the pharmaceutical composition of the present disclosure can be applied may be any eye disease known in the art, such as a retinal disease, a macular disease, a choroidal disease, etc. without special limitation. For example, it may be one or more disease selected from ocular neovascularization, macular degeneration, maculopathy, macular edema, retinal degeneration, retinal edema, retinopathy, macula tumentia and glaucoma. Specifically, it may be one or more selected from macular degeneration, macular edema, retinal degeneration, retinal edema and diabetic retinopathy (DR). More specifically, it may be one or more disease selected from retinal degeneration, retinal edema, macular degeneration and diabetic retinopathy (DR). In addition, the macular degeneration may be age-related macular degeneration (AMD).

In the present specification, the term "macular degeneration" refers to any number of disorders and conditions in which the macula becomes degenerated or lose functional activity. The degeneration or loss of functional activity may occur as a result of, for example, apoptosis, reduced cell proliferation, loss of normal biological function or a combination thereof. Macular degeneration can lead to and/or manifest as change in the structural integrity of cells and/or the extracellular matrix of the macula, change in the composition of normal cells and/or the extracellular matrix and/or loss of function of macular cells. The cells may be any type of cells normally present in or near the macula, including RPE cells, photoreceptor cells and/or capillary endothelial cells. Age-related macular degeneration (AMD) is the most common macular degeneration, but the term "macular degeneration" does not necessarily exclude macular degeneration in non-elderly patients. Non-limiting examples of macular degeneration include age-related macular degeneration (wet or dry), Best's macular dystrophy, Sorsby's fundus dystrophy, malattia leventinese, Doyne's honeycomb retinal dystrophy, Stargardt disease (also called Stargardt macular dystrophy, juvenile macular degeneration or fundus flavimaculatus) and macular degeneration related with desquamation of the pigment epithelium.

In the present specification, the term "age-related macular degeneration" (AMD) refers to a retinopathy that commonly affects the elderly and is associated with the loss of central vision caused by damage to the central part of the retina (i.e., the macula). AMD is generally characterized by the progressive accumulation or aggregation of yellowish insoluble extracellular deposits called drusen (accumulation of extracellular proteins and lipids such as amyloid beta) within the macula (mainly between the retinal pigment epithelium (RPE) and the underlying choroid). The accumulation or aggregation of these deposits in the macula can gradually deteriorate the macula, resulting in damage to the central vision. The term "macula" used in the present specification refers to the central part of the retina, which is responsible for the central, high-resolution, color vision.

Although several theories have been proposed, including oxidative stress, mitochondrial dysfunction and inflammatory processes, the etiology of age-related macular degeneration is not understood well. The imbalance between the production and degradation of damaged cellular components leads to the accumulation of harmful products, for example, intracellular lipofuscin and extracellular drusen. Incipient atrophy is demarcated by areas of retinal pigment epithelium (RPE) thinning or depigmentation that precede geographic atrophy in the early stages of AMD. In advanced stages of AMD, atrophy of the RPE (geographic atrophy) and/or development of new blood vessels (neovascularization) result in the death of photoreceptors and central vision loss. In the dry (nonexudative) AMD, drusen accumulates between the retina and the choroid. In the wet (exudative) AMD, which is more severe, blood vessels grow up from the choroid (neovascularization) behind the retina which can leak exudate and fluid and also cause hemorrhaging.

The age-related macular degeneration can be divided into dry (atrophic) macular degeneration and wet (neovascular or exudative) macular degeneration. The age-related macular degeneration can also be divided into early AMD, intermediate AMD, and late or advanced AMD (geographic atrophy).

In the present specification, the term "dry AMD" (also called atrophic age-related macular degeneration or nonexudative AMD) refers to all types of AMD which are not wet (neovascular) AMD. It includes early and intermediate forms of AMD, as well as the advanced form of dry AMD known as geographic atrophy. Dry AMD patients tend to have minimal symptoms in the earlier stages; visual function loss occurs more often if the condition advances to geographic atrophy.

In the present specification, the term "wet AMD" (also called neovascular age-related macular degeneration or exudative AMD) refers to retinal symptoms characterized by the presence of retinal neovascularization, and is the most advanced form of AMD. In wet AMD, the blood vessels grow from the choroidal capillaries and, in some cases, from the underlying retinal pigment epithelium (choroidal neovascularization or neovascularization) through Bruch's membrane. The organization of serous or hemorrhagic exudates escaping from these blood vessels results in fibrovascular scarring of the macular region with attendant degeneration of the neuroretina, detachment and tears of the retinal pigment epithelium, vitreous hemorrhage and permanent loss of central vision.

In the present specification, the term "retinopathy" refers to the disease, inflammation or damage of the retina (i.e., the tissues lining the inner surface of the back of the eye that captures images passing through the cornea and the eye lens). The retinopathy includes diabetic retinopathy, central retinopathy, and retinopathy of prematurity.

In the present disclosure, the term "diabetic retinopathy" includes non-proliferative diabetic retinopathy (NPDR), proliferative diabetic retinopathy (PDR), diabetic maculopathy, diabetic macular edema and diabetic retinal edema.

The term "maculopathy" used in the present specification refers to any pathological symptom of the macula which is the central region of the retina associated with highly sensitive and precise vision. In some embodiments, the term "maculopathy" and "retinopathy" may be used interchangeably (i.e., only when the macula is affected). In some embodiments, the maculopathy is diabetic maculopathy.

The "diabetic maculopathy" occurs when the macula is affected by retinal changes caused by diabetes. The term refers to two distinct eye diseases: diabetic macular edema and diabetic ischemic maculopathy. Both types of maculopathy are often comorbid, i.e., people with macular edema often also have ischemic maculopathy. Ischemic maculopathy occurs with macular edema and may occur even when the macular edema is mild. In some embodiments, the retinal changes associated with diabetic maculopathy include reduction of retinal potential within the retina of the subject, loss of pericytes, formation of acellular capillaries, vascular congestion, vascular dysfunction, vascular leakage, vascular occlusion, tissue swelling (edema), tissue ischemia, or any combination thereof.

In the present specification, the term "ocular neovascularization" refers to the abnormal growth of blood vessels in different parts of the eye that can induce hemorrhage and cause vision loss. In the present specification, the term "choroid neovascularization" refers to the abnormal growth of new blood vessels in the choroid (i.e., the vascular layer of the eye that includes connective tissues and lies between the retina and the sclera). In wet AMD, new blood vessels can grow into the retina through the retinal pigment epithelium (RPE) and the choroid, and can damage visual function through blood and lipid leakage. In the present specification, the term "retinal neovascularization" refers to the abnormal development, proliferation and/or growth of blood vessels on or with the retina, for example, on the surface of the retina. The retinal neovascularization may occur in many retinopathies such as retinopathy associated with retinal ischemia and/or inflammatory diseases (e.g., diabetic retinopathy, sickle cell retinopathy, Eales disease, ocular ischemic syndrome, carotid-cavernous fistula, familial exudative vitreoretinopathy, hyperviscosity syndrome, idiopathic obstructive arteriolitis, radiation retinopathy, retinal vein occlusion, retinal artery occlusion, retinal artery occlusion, birdshot retinochoroidopathy, retinal vasculitis, sarcoidosis, toxoplasmosis, uveitis, choroidal melanoma, chronic retinal detachment, anterior ischemic optic neuropathy (AION), non-arteritic anterior ischemic optic neuropathy (NAION) and incontinentia pigmenti).

In the present specification, the term "optic nerve damage" refers to the change in the normal structure or function of the optic nerve. The change in the normal structure or function of the optic nerve can be the result of any disease, disorder or injury, including glaucoma. The change in the normal function of the optic nerve includes any change in the proper functional ability of the optic nerve such as the ability to transmit visual information from the retina to the brain. The functional change may manifest, for example, as visual field loss, central vision impairment, abnormal color vision, etc. Examples of the structural change include loss of retinal nerve fibers, abnormal cupping of the optic nerve and/or loss of cells from the retinal ganglion cell layer. The term "optic nerve damage" used in the present specification may include the damage to one or more optic nerve of the subject.

The pharmaceutical composition according to the present disclosure may contain the (7S)-(+)-cyclopentylcarbarmic acid, 8,8-dimethyl-2-oxo-6,7-dihydro-2H,8H-pyrano[3,2-g]chromen-7-yl-ester or a pharmaceutically acceptable salt thereof alone or may further contain one or more pharmaceutically acceptable carrier, excipient or diluent.

The pharmaceutically acceptable carrier may include, for example, a carrier for oral administration or a carrier for parenteral administration. The carrier for oral administration may include lactose, starch, a cellulose derivative, magnesium stearate, stearic acid, etc. And, the carrier for parenteral administration may include water, a suitable oil, physiological saline, water-soluble glucose, glycol, etc. and may further include a stabilizer and a preservative. Suitable stabilizers include sodium bisulfite, sodium sulfite or an antioxidant such as ascorbic acid. Suitable preservatives include benzalkonium chloride, methyl- or propylparaben and chlorobutanol. The pharmaceutical composition of the present disclosure may further contain, in addition to the above-described ingredients, a lubricant, a wetting agent, a sweetener, a flavoring agent, an emulsifier, a suspending agent, etc. For other pharmaceutically acceptable carriers, reference may be made to those described in the following literature: Remington's Pharmaceutical Sciences, 19th ed., Mack Publishing Company, Easton, PA, 1995.

The composition of the present disclosure may be administered to a mammal including human by any method. For example, it can be administered orally or parenterally. Methods for parenteral administration include, but are not limited to, intravenous administration, intramuscular administration, intraarterial administration, intramedullary administration, intradural administration, intraocular injection, intravitreal injection, subretinal injection, suprachoroidal injection, eye drop administration, transdermal administration, subcutaneous administration, intraperitoneal administration, intranasal administration, enteral administration, topical administration, sublingual administration or intrarectal administration, specifically intraocular injection, intravitreal injection, subretinal injection, suprachoroidal injection or eye drop administration, more specifically eye drop administration.

The pharmaceutical composition of the present disclosure may be prepared into a formulation for oral administration or parenteral administration depending on the above-described administration routes.

For oral administration, the composition of the present disclosure may be formulated into a powder, a granule, a tablet, a pill, a sugar-coated tablet, a capsule, a liquid, a gel, a syrup, a slurry, a suspension, etc. using methods known in the ar. For example, after mixing the active ingredient with a solid excipient, pulverizing the mixture and adding a suitable adjuvant, the mixture may be processed into a granule to obtain a tablet or a sugar-coated tablet. Examples of suitable excipients may include sugars including lactose, dextrose, sucrose, sorbitol, mannitol, xylitol, erythritol, maltitol, etc., starches including corn starch, wheat starch, rice starch, potato starch, etc., celluloses including cellulose, methyl cellulose, sodium carboxymethyl cellulose, hydroxy-propylmethyl cellulose, etc. and fillers such as gelatin, polyvinylpyrrolidone, etc. In addition, crosslinked polyvi-nylpyrrolidone, agar, alginic acid, sodium alginate, etc. may be added as a disintegrant if desired. Furthermore, the pharmaceutical composition of the present disclosure may further contain an anticoagulant, a lubricant, a wetting agent, a flavoring agent, an emulsifier, an antiseptic, etc.

As formulations for parenteral administration, an injec-tion, an eye drop, an ointment, a cream, a lotion, an oil, a gel, an aerosol or a nasal inhalant may be prepared by methods known in the art. These formulations are described in Remington's Pharmaceutical Science (15th edition, 1975. Mack Publishing Company, Easton, Pennsylvania 18042, Chapter 87: Blaug, Seymour), which is generally known in pharmaceutical chemistry.

Specifically, the pharmaceutical composition of the pres-ent disclosure may be prepared into any formulation selected from an oral medication, an injection, an eye drop and an ointment. More specifically, it may be prepared into any of an ophthalmic injection, an eye drop and an ointment, which are formulations for topical administration to the eye, further more specifically into an eye drop.

The pharmaceutical composition of the present disclo-sure, which contains an effective amount of (7S)-(+)-cyclo-pentylcarbarmic acid, 8,8-dimethyl-2-oxo-6,7-dihydro-2H, 8H-pyrano[3,2-g]chromen-7-yl-ester or a pharmaceutically acceptable salt thereof, may provide the effect of preventing, alleviating or treating an eye disease. In the present speci-fication, the 'effective amount' refers to an amount which exhibits a higher response as compared to a negative control group, specifically an amount sufficient to alleviate or treat an eye disease. The (7S)-(+)-cyclopentylcarbarmic acid, 8,8-dimethyl-2-oxo-6,7-dihydro-2H,8H-pyrano[3,2-g] chromen-7-yl-ester or a pharmaceutically acceptable salt thereof may be contained in the pharmaceutical composition at a concentration of 0.01-20 mg/mL, specifically 0.05-15 mg/mL, more specifically 0.1-10 mg/mL, more specifically 0.5-5 mg/mL, more specifically 1-2 mg/mL, most specifi-cally 1.5 mg/mL. If the content of the (7S)-(+)-cyclopen-tylcarbarmic acid, 8,8-dimethyl-2-oxo-6,7-dihydro-2H,8H-pyrano[3,2-g]chromen-7-yl-ester is below the lower limit, cell viability may be superior, but the effect of alleviating or treating an eye disease may not be achieved as desired. Conversely, if it exceeds the upper limit, the effect of alleviating or treating an eye disease may not increase as much as the concentration or toxicity may occur. As a result of in-vitro experiments, when the concentration of the (7S)-(+)-cyclopentylcarbarmic acid, 8,8-dimethyl-2-oxo-6, 7-dihydro-2H,8H-pyrano[3,2-g]chromen-7-yl-ester of the present disclosure was within the above range, side effects such as cytotoxicity, etc. were not observed while a signifi-cant effect was exhibited for the alleviation or treatment of an eye disease. The effective amount of the (7S)-(+)-cyclo-pentylcarbarmic acid, 8,8-dimethyl-2-oxo-6,7-dihydro-2H, 8H-pyrano[3,2-g]chromen-7-yl-ester contained in the phar-maceutical composition of the present disclosure will vary depending on the type of the composition, etc.

The total effective amount of the pharmaceutical compo-sition of the present disclosure can be administered to a patient with a single dose or according to a fractionated treatment protocol in which multiple doses are administered over a long period of time. The content of the active ingredient in the pharmaceutical composition of the present disclosure may be varied depending on the severity of a disease.

An appropriate administration dosage of the pharmaceu-tical composition varies depending on factors such as for-mulation method, administration method, the age, body weight, sex, pathological condition and diet of a patient, administration time, administration route, excretion rate and response sensitivity, and an administration dosage effective for the desired treatment or alleviation can be easily deter-mined and prescribed by an ordinarily trained physician. In a specific exemplary embodiment, a preferred daily admin-istration dosage of the pharmaceutical composition may be 10-200 µL/kg.

The present disclosure also provides a health functional food for preventing or alleviating an eye disease, which contains (7S)-(+)-cyclopentylcarbarmic acid, 8,8-dimethyl-2-oxo-6,7-dihydro-2H,8H-pyrano[3,2-g]chromen-7-yl-ester as an active ingredient.

The compound of the present disclosure may be prepared into a sitologically acceptable salt according to a common method in the art.

The 'health functional food' of the present disclosure refers to a food prepared (including processing) in accor-dance with legal standards using raw materials or ingredi-ents with useful functionality for the human body (Article 3, Subparagraph 1 of the Health Functional Food Act). The 'health functional food' may be different in terminology or scope from country to country, but may correspond to the 'dietary supplement' in the US, the 'food supplement' in Europe, the 'health functional food' or 'food for special health use (FoSHU)' in Japan, the 'health food' in China, etc.

The health functional food may further contain a food additive and the suitability as the food additive conforms to the general rules and general test methods of the 'Food Additives Code' unless specified otherwise.

In addition, the health functional food may be prepared into a health functional food for preventing or alleviating an eye disease using, together with the (7S)-(+)-cyclopentyl-carbarmic acid, 8,8-dimethyl-2-oxo-6,7-dihydro-2H,8H-pyrano[3,2-g]chromen-7-yl-ester, a health functional food material helpful for the eye health such as lutein, zeaxanthin, bilberry extract, marigold flower extract, blueberry fruit extract, perilla extract, haematococcus extract, etc., which are notified as 'functional raw materials' or individually recognized for use in "health functional foods for improving eye health".

The health functional food refers to a food prepared by adding the (7S)-(+)-cyclopentylcarbarmic acid, 8,8-dim-ethyl-2-oxo-6,7-dihydro-2H,8H-pyrano[3,2-g]chromen-7-yl-ester of the present disclosure to various food materials or preparing the same into a capsule, a powder, a suspension, etc., which brings specific health effects when ingested and is advantageous in that it has no side effect that may occur during the long-term medication of a drug because it is based on food materials. The health functional food of the present disclosure obtained in this way is very useful because it can be ingested on a daily basis. The addition amount of the (7S)-(+)-cyclopentylcarbarmic acid, 8,8-dimethyl-2-oxo-6, 7-dihydro-2H,8H-pyrano[3,2-g]chromen-7-yl-ester in the health functional food is usually 0.01-50 wt %, specifically 0.1-10 wt %, although it can vary depending on the type of the health functional food within a range that does not impair the original taste of the food. In addition, when the health functional food is in the form of a pill, a granule, a tablet or a capsule, the compound may be added in an amount of usually 0.1-100 wt %, specifically 0.5-50 wt %. In a specific exemplary embodiment, the health functional food of the present disclosure may be in the form of a powder, a granule, a tablet, a capsule or a beverage.

In addition, the health functional food may be prepared into various forms by common methods known in the art. General foods include, but are not limited to, beverages (including alcoholic beverages), fruits and processed foods thereof (e.g., canned fruits, bottled fruits, jam, marmalade, etc.), fish, meat and processed foods thereof (e.g., ham, sausage, corned beef, etc.), breads, noodles (e.g., udon, buckwheat noodles, ramen, spaghetti, macaroni, etc.), fruit juice, various drinks, cookies, taffy, dairy products (e.g., butter, cheese, etc.), edible vegetable oils, margarine, vegetable proteins, retort foods, frozen foods, various seasonings (e.g., soybean paste, soy sauce, sauce, etc.), etc. and may be prepared by adding the (7S)-(+)-cyclopentylcarbarmic acid, 8,8-dimethyl-2-oxo-6,7-dihydro-2H,8H-pyrano[3,2-g]chromen-7-yl-ester. In addition, nutritional supplements include, but are not limited to, a capsule, a tablet, a pill, etc. and may be prepared by adding the (7S)-(+)-cyclopentyl-carbarmic acid, 8,8-dimethyl-2-oxo-6,7-dihydro-2H,8H-pyrano[3,2-g]chromen-7-yl-ester. In addition, as the health functional food, for example, the (7S)-(+)-cyclopentylcar-barmic acid, 8,8-dimethyl-2-oxo-6,7-dihydro-2H,8H-pyrano[3,2-g]chromen-7-yl-ester itself may be prepared into a tea, a juice or a drink for drinking (health beverages), or may be prepared into a granule, a capsule or a powder. In addition, the (7S)-(+)-cyclopentylcarbarmic acid, 8,8-dim-ethyl-2-oxo-6,7-dihydro-2H,8H-pyrano[3,2-g]chromen-7-yl-ester may be prepared into a powder or a concentrated extract for use as a food additive.

When the health functional food for preventing or alleviating an eye disease of the present disclosure is used as a health beverage composition, the health beverage composition may further contain various flavoring agents, natural carbohydrates, etc. as additional ingredients as in common beverages. The aforementioned natural carbohydrates include monosaccharides such as glucose and fructose; disaccharides such as maltose and sucrose; polysaccharides such as dextrin and cyclodextrin; sugar alcohols such as xylitol, sorbitol, erythritol, etc. As the sweetener, a natural sweetener such as thaumatin and stevia extract; a synthetic sweetener such as saccharin and aspartame, etc. may be used. The content of the natural carbohydrate may be usually about 0.01-0.04 g, specifically about 0.02-0.03 g per 100 mL of the composition of the present disclosure.

The (7S)-(+)-cyclopentylcarbarmic acid, 8,8-dimethyl-2-oxo-6,7-dihydro-2H,8H-pyrano[3,2-g]chromen-7-yl-ester of the present disclosure may be contained in the health functional food as an active ingredient in an amount effective for achieving the effect of preventing, alleviating or treating an eye disease. Specifically, the (7S)-(+)-cyclopen-tylcarbarmic acid, 8,8-dimethyl-2-oxo-6,7-dihydro-2H,8H-pyrano[3,2-g]chromen-7-yl-ester may be contained at a concentration of 0.01-20 mg/mL, specifically 0.05-15 mg/mL, more specifically 0.1-10 mg/mL, more specifically 0.5-5 mg/mL, more specifically 1-2 mg/mL, most specifically 1.5 mg/mL, based on the total content of the health functional food. If the content of the (7S)-(+)-cyclopentylcarbarmic acid, 8,8-dimethyl-2-oxo-6,7-dihydro-2H,8H-pyrano[3,2-g] chromen-7-yl-ester is below the lower limit, cell viability may be superior, but the effect of alleviating or treating an eye disease may not be achieved as desired. Conversely, if it exceeds the upper limit, the effect of alleviating or treating an eye disease may not increase as much as the concentration or toxicity may occur.

Hereinafter, the present disclosure will be described in more detail through specific examples. However, the following examples are provided to describe the present disclosure more specifically and it will be obvious to those having ordinary knowledge in the art that the scope of the present disclosure is not limited by them.

EXAMPLE (1) Preparation of (7S)-(+)-cyclopentylcarbarmic acid 8,8-dimethyl-2-oxo-6,7-dihydro-2H,8H-pyrano[3,2-g]chromen-7-yl-ester After dissolving (+)-(3S)-3-hydroxy-2,2-dimethyl-3,4-di-hydropyrano[3,2-g]chromen-8-one (200 mg, 0.812 mmol) in 20 mL of dry methylene chloride (MC) in a round flask, cyclopentyl isocyanate (1.827 mmol), triethylamine (TEA, 204 μL, 1.462 mmol) and 4-(dimethylamino)pyridine (DMAP, 59.5 mg, 0.487 mmol) were added and reaction was conducted at 40° C. for 24 hours. The reaction solution was concentrated under reduced pressure and the obtained residue was purified by silica gel column separation to obtain the target compound (CGK012).

Yield: 43.2%;

White solid;

mp: 158.5° C.;

$R_f$=0.41 (n-HX:EA=1:1);

$[\alpha]_D^{24}$ +29.0533 (c=3, CHCl$_3$);

$^1$H NMR (400 MHz, DMSO-d$_6$): 7.920 (d, J=9.6 Hz, 1H), 7.475 (s, 1H), 7.254 (d, J=7.2 Hz, 1H), 6.759 (s, 1H), 6.253 (d, J=9.6 Hz, 1H), 4.902 (t, J=3.8 Hz, 1H), 3.827-3.734 (m, 1H), 3.182 (dd, J=4.4, 17.6 Hz, 1H), 2.810 (dd, J=3.2, 17.6 Hz, 1H), 1.768-1.701 (m, 2H), 1.591-1.511 (m, 3H), 1.484-1.390 (m, 3H), 1.334 (s, 3H), 1.279 (s, 3H);

IT-TOF/MS 380.1468 [M+Na]$^+$.

(2) Preparation of Eye Drop

An eye drop was prepared with the composition described in Table 1 according to a common eye drop preparation method.

TABLE 1

| Ingredients | Contents (wt %) |
|---|---|
| Compound of Example (1) | 1.5 mg/mL |
| Polyoxylethylene hydrogenated castor oil | 0.50 |
| Polyoxyl 35 hydrogenated castor oil | 5.00 |
| Polyoxyl 40 hydrogenated castor oil | 1.00 |
| Propylene glycol dicaprylate | 0.05 |
| Medium-chain triglyceride | 0.35 |
| Polyoxyl-15-hydroxysterate | 0.25 |
| Tyloxapol | 0.30 |
| Polysorbate 80 | 4.00 |
| Disodium edetate hydrate | 0.10 |
| Benzalkonium chloride | 0.01 |
| Poloxamer 407 | 2.00 |
| Hydroxylpropyl β-cyclodextrin | 5.00 |
| Sulfobutyl ether β-cyclodextrin | 5.00 |
| Distilled water | Balance |
| Total | 100 |

Comparative Example

An eye drop was prepared in the same manner as in Example using decursin instead of the compound of Example (1) (CGK012).

<Materials and Experimental Methods>

(1) Cell Culturing

ARPE-19 cells (RID: CVCL 0145) and L-Wnt3a cells (RID: CVCL 0635) were acquired from American Type Culture Collection (ATCC) and cultured in a DMEM medium supplemented with 10% fetal bovine serum (FBS), 120 μg/mL penicillin and 200 μg/mL streptomycin. Human umbilical vein endothelial cells (HUVECs, RID: CVCL 2959) were purchased from CEFO (Cell Engineering for Origin) and cultured using an optimized medium (CEFOgro-HUVEC). Wnt3a-CM (Wnt3a-conditioned medium) was prepared using L-Wnt3a cells that secrete the Wnt-3a protein into the medium. First, the cells were cultured for 4 days and the medium was recovered and replaced with a fresh medium. After culturing for 3 days, the medium was recovered. The two media were combined and used after passing through a 0.22-μm filter. All the cells were cultured in a cell incubator under the condition of 37° C. and 5% $CO_2$.

(2) Cell Viability Test

HUVECs were inoculated into a 96-well plate with a transparent black bottom at 5,000 cells per well, incubated overnight, and then treated with a test substances (compound of Example (1) (CGK012) or decursin of Comparative Example (1)) at various concentrations together with a medium (total volume per well: 100 μL). After 48 hours, cell viability was measured using a CELLTITER-GLO® luminescent cell viability assay kit (Promega, G7572) according to the manufacturer's instructions. After treatment with CGK012 or decursin, the plate was stabilized at room temperature for 30 minutes and then 100 μL of a CELLTI- (4) Animal Experiments 1) Obtainment of Animals After obtaining 50 male Chinchilla rabbits weighing about 2.5-3.0 kg from DREAMBIO, their health status was checked during a 7-day acclimatization period, and healthy animals were used in the test.

2) Induction of CNV (Choroidal Neovascularization)

After the acclimatization period, 42 healthy rabbits were selected and a mydriatic agent (MIDRIACIL™ 1% eye drop) was instilled into the right eye. After anesthetizing the animals, laser (ELITE, LUMENIS, USA) was irradiated under the condition of 532 nm, power 150 mW and duration 0.1 sec, and 6 spots were made in about 6 o'clock direction around the optic nerve.

3) Administration of Test Substances

After dividing the test animals into a total of 7 groups, G1 to G7, administration of the test substance was started on the day of the CNV induction using laser with the concentrations described in Table 2. In Table 2, EYLEA™ (Aflibercept) was used as a positive control substance. For intravitreal injection, 40 μL of the positive control substance (EYLEA™) was injected intravitreally into the right eye of the animal in the anesthetized state using a syringe equipped with a 31-gauge needle on the day of the CNV induction. For instillation, after the animal was taken out of the cage and corrected naturally by an assistant, 200 μL of the test substance was instilled into the center of the cornea of the right eye by using a pipette. In the case of "a)", the instillation was divided into 4 times and each administration was spaced by 5 minutes.

TABLE 2

| Group | Sex | No. of animals | Administered substance | Administration route | Administration dosage (μg/eye) | Administered volume (μL/eye/) | No. of administration |
|---|---|---|---|---|---|---|---|
| G1 | M | 6 | Vehicle | Instillation | 0 | 200[a)] | 2/day |
| G2 | M | 6 | EYLEA ™ | Intravitreal | 1600 | 40 | 1/3 weeks |
| G3 | M | 6 | EYLEA[+ ™] + CGK012 | Intravitreal + instillation | 1600 + 300 | 40 + 200[a)] | 1/6 weeks + 2/day |
| G4 | M | 6 | EYLEA ™ + CGK012 | Intravitreal + instillation | 800 + 300 | 20 + 200[a)] | 1/3 weeks + 2/day |
| G5 | M | 6 | CGK012 | Instillation | 300 | 200[a)] | 2/day |
| G6 | M | 6 | CGK012 low | Instillation | 300 | 200[a)] | 1/day |
| G7 | M | 6 | Decursin | Instillation | 300 | 200[a)] | 1/day |

TER-GLO® reagent (the same volume as the medium) was added to each well. After mixing in an orbital shaker for 2 minutes for cell lysis, stabilization was induced at room temperature for 10 minutes, and then luminescence was measured. Cell viability was calculated by subtracting the luminescence value before the treatment with CGK012 or decursin from the measured luminescence value, and was expressed as a relative value with respect to the value before the treatment with CGK012 or decursin as 100%.

(3) Western Blotting

Whole cell proteins were obtained using a RIPA buffer. After treating the cells with an appropriate amount of a RIPA buffer supplemented with 1× protease inhibitor, the cells were reacted on ice while vortexing once every 10 minutes. After centrifuging at 13,000 rpm and at 4° C. for 10 minutes and quantifying the obtained supernatant by BRADFORD™ assay, 20 μL of proteins were separated according to molecular weight through electrophoresis. Then, they were transferred to a PVDF membrane and the level of the proteins was investigated using antibodies against VEGF (sc-152, 1:500) and β-actin (A1978, 1:2000; Sigma).

4) Fluorescein Angiography for Measurement of CNV

Before the administration of the test substance (0) and on 7, 14, 28, 42 and 56 days after the administration, a mydriatic agent (MIDRIACIL™ 1% eye drop) was instilled into the right of the animal. Then, after anesthetizing the animal and injecting about 1 mL of a 2% fluorescein sodium salt solution via the ear vein, images were taken within about 2 minutes using a fundus camera (TRC-50IX, Topcon, Japan).

Analysis of Fluorescein Intensity

Retinal CNV and drug efficacy were confirmed using the retinal fluorescein fundus images. The fluorescein intensity of the irradiation area was analyzed using the ImageJ software (NIH, Bethesda, MD).

5) Statistical Analysis

For the results of this test, the significance between the test groups was tested using parametric one-way ANOVA assuming the normality of the data. When significance was recognized, a post hoc test was performed using Dunnett's multiple comparison test. Statistical analysis was performed <table>
<tr><td>15</td><td>16</td></tr>
</table> using PRISM 7.04 (GraphPad Software Inc., San Diego, CA, USA), and $p < 0.05$ was considered statically significant.

Test Example 1: Comparison of Efficacy of Compound of Example (CGK012) vs Compound of Comparative Example (Decursin)

1-1: In-Vitro Test

Figure 1B:
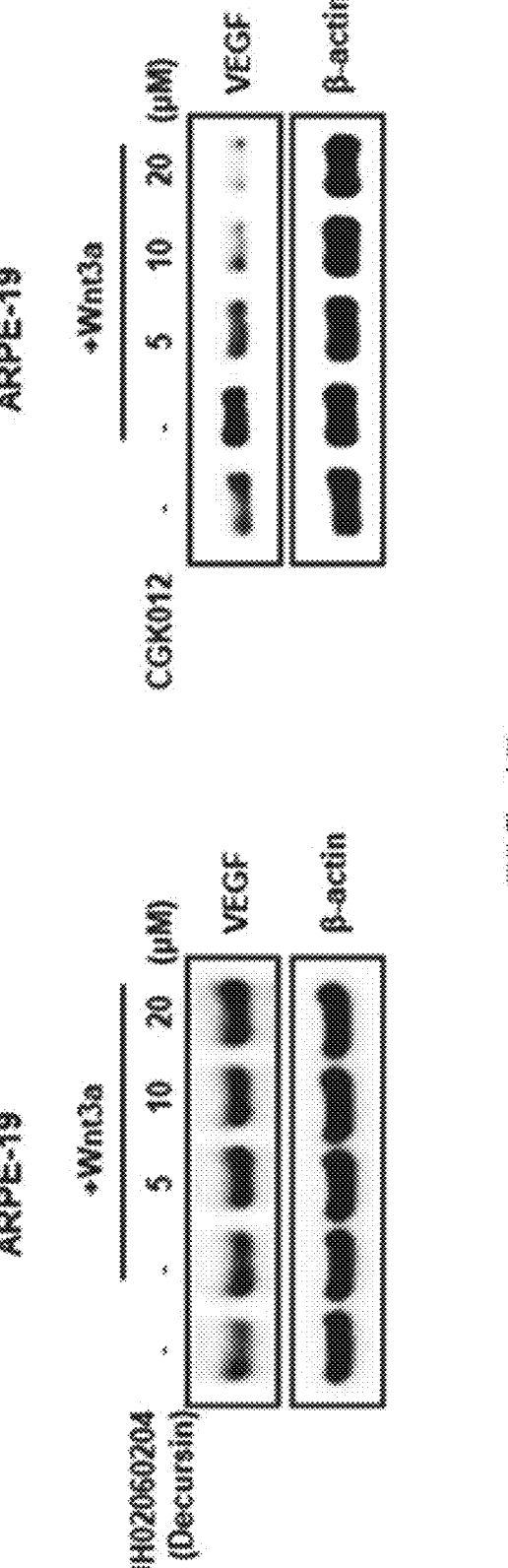

FIGS. 1A and 1B show a result of investigating the effect of the compound of the example (CGK012) and the compound of the comparative example (decursin) on the cell viability of human endothelial cells (HUVECs) (FIG. 1A) and the level of vascular endothelial growth factor (VEGF) in human retinal pigment epithelial cells (ARPE-19 cells) (FIG. 1B).

From FIG. 1A, it can be seen that the CGK012 compound of the example of the present disclosure induced the apoptosis of the human endothelial cells (HUVECs) in a concentration-dependent manner and significantly inhibited the survival of the HUVECs at high concentrations, whereas the decursin compound of the comparative example did not significantly induce the apoptosis of the HUVECs even at high concentrations.

In addition, referring to FIG. 1B, whereas the CGK012 compound of the example of the present disclosure remarkably decreased VEGF in human retinal pigment epithelial cells (ARPE-19) in a concentration-dependent manner, the decursin compound of the comparative example did not show significant effect on the level of VEGF.

This result suggests that the CGK012 compound of the present disclosure regulates the level of VEGF unlike the decursin that mediates VEGFR-2.

1-2: In-Vivo Test

Figure 2A:
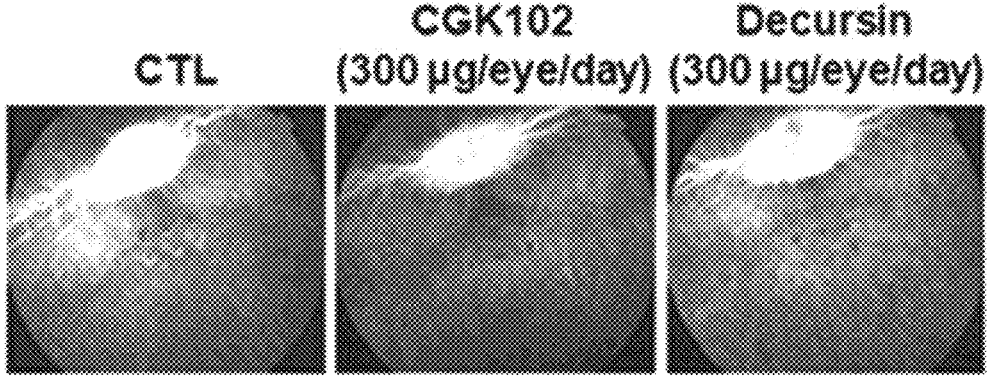
FIG. 2A shows a result of investigating the effect of the dropping of a compound of the present disclosure (CGK012) on the eye on the inhibition of intraocular vascular leakage in a choroidal neovascularization (CNV)-induced rabbit model by fluorescein angiography.

The test substance of the example or the comparative example was dropped onto the eye of a rabbit wherein choroidal neovascularization (CNV) was induced by laser irradiation, for 7 days, 300 µg per each administration. On day 7 after the start of the test substance administration, the eye was imaged with a fundus camera to compare the effect of the test substance on intraocular vascular leakage and the fluorescence intensity of the retina was analyzed. The result is shown in Table 3 and FIGS. 2A and 2B. FIG. 2A shows the result of investigating the effect of the dropping of the compound of the present disclosure (CGK012) on the eye on the inhibition of intraocular vascular leakage in the choroidal neovascularization (CNV)-induced rabbit model by fluorescein angiography, and FIG. 2B shows the result of

TABLE 3

| | | Substance | Fluorescence intensity (% of control group) |
|---|---|---|---|
| Control group | G1 | Placebo | 100 |
| Test group | G6 | Example (CGK012) | 75.52 ± 3.93 |
| Comparison group | G7 | Comparative Example (decursin) | 95.66 ± 10.80 |

Figure 2B:
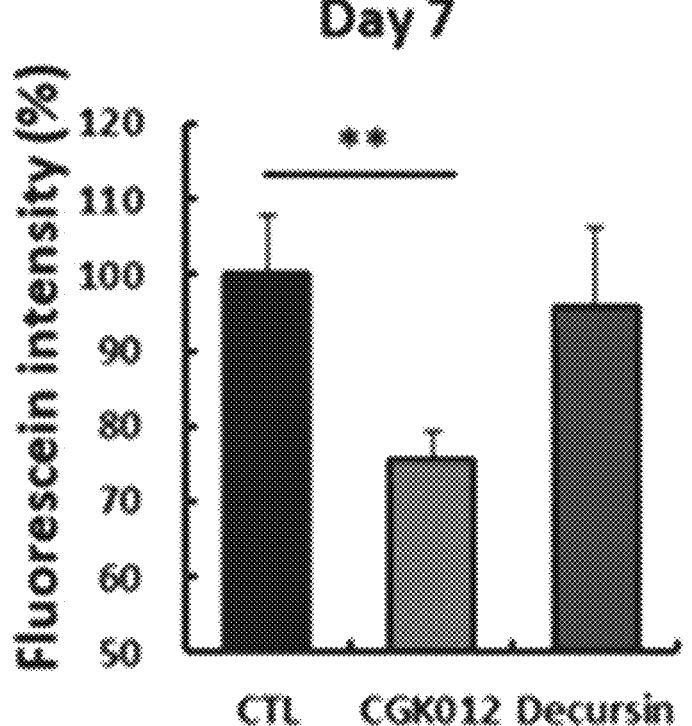
FIG. 2B shows a result of comparing the fluorescence intensity in FIG. 2A with a control group.

From Table 3 and FIGS. 2A and 2B, it can be seen that the retinal fluorescence intensity was decreased significantly for the test group as compared to the control group, whereas the comparison group showed a level comparable to that of the control group.

This result suggests that the CGK012 compound of the example of the present disclosure, which can be administered conveniently as compared to oral administration or intravitreal injection, has superior activity of inhibiting activity of inhibiting intraocular vascular leakage.

Test Example 2: Comparison of Single Administration of Compound of Example (CGK012) and Co-Administration with Positive Control Eylea

2-1: Comparison of Effect with Positive Control EYLEA™

Figure 3:
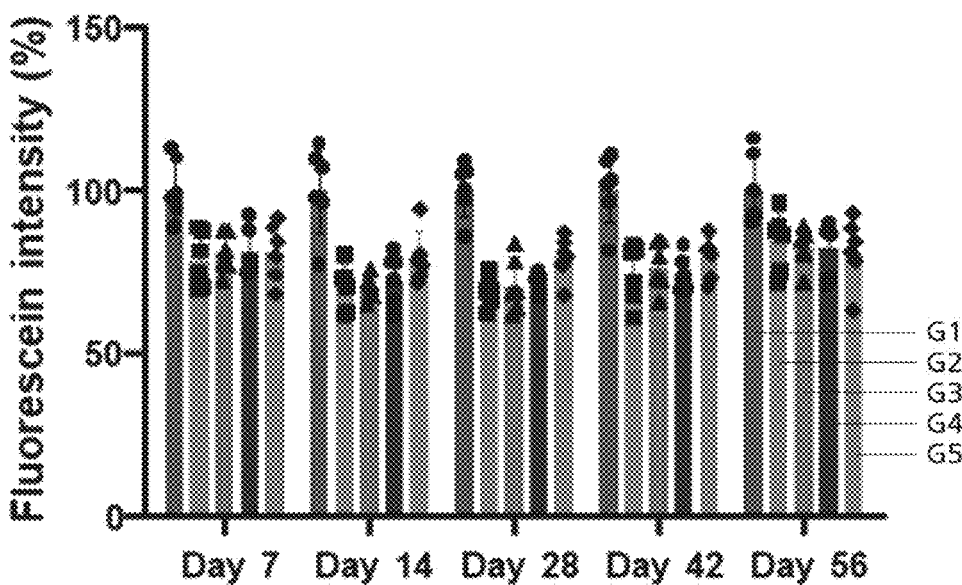
FIG. 3 shows a result of administering test substances to a choroidal neovascularization (CNV)-induced mouse model and comparing the fluorescence intensity of test groups G1 to G5 over time after the start of the administration with a control group.

For a rabbit wherein choroidal neovascularization (CNV) was induced by laser irradiation, EYLEA™ was intravitreally injected as a positive control, the eye drop of the example was administered by dropping onto the eye or EYLEA™ and the eye drop of the example were co-administered. Specifically, the test substances were administered to the test groups as described in Table 2: (G1) induced control group (treated with vehicle), (G2) EYLEA™ (positive control group), (G3) EYLEA™+ CGK012 administration group (administration interval of Eylea increased as compared to G2 (3 weeks→6 weeks)), (G4) EYLEA™+CGK012 administration group (administration dosage of Eylea decreased as compared to G2 (1600 µg→800 µg), (G5) CGK012 single administration group. On days 7, 14, 28, 42 and 56 after the administration of the test substance, the level of retinal fluorescence intensity was analyzed and the result is shown in Table 4 and FIG. 3. FIG. 3 shows the result of administering test substances to the choroidal neovascularization (CNV)-induced mouse model and comparing the fluorescence intensity of the test groups G1 to G5 over time after the start of the administration with the control group. Table 4 compares the relative fluorescence intensity (% of control group) of the test groups G1 to G5 over time after the start of the administration.

TABLE 4

| | Day 7 | Day 14 | Day 28 | Day 42 | Day 56 |
|---|---|---|---|---|---|
| G1 | 100.000 ± 9.353 | 100.000 ± 13.296 | 100.000 ± 8.425 | 100.000 ± 10.592 | 100.000 ± 10.895 |
| G2 | 78.474 ± 8.452*** | 70.022 ± 7.008*** | 69.348 ± 5.013*** | 74.154 ± 9.129*** | 84.087 ± 9.079* |
| G3 | 80.530 ± 6.134** | 70.057 ± 3.755*** | 70.531 ± 8.406*** | 76.445 ± 7.535*** | 82.081 ± 6.174** |
| G4 | 80.677 ± 7.246** | 72.560 ± 7.894*** | 71.265 ± 3.038*** | 73.994 ± 5.251*** | 82.077 ± 8.164** |
| G5 | 80.877 ± 8.905 | 79.116 ± 7.972* | 79.152 ± 6.642* | 79.137 ± 6.355* | 81.041 ± 10.391** | comparing the fluorescence intensity in FIG. 2A with the control group. Table 3 compares the relative fluorescence intensity (% of control group) of the irradiation area determined by analyzing the retinal fluorescein angiographic images of the control group (G1), the test group (G6) and the comparison group (G7).

In Table 4, *,  and * indicate significant difference from the group G1 with $p < 0.05$, $p < 0.01$ and $p < 0.001$, respectively.

From Table 4 and FIG. 3, it can be seen that the test groups G2 to G5 showed decreased neovascularization by 20-30% as compared to the induced control group G1. The test groups G2 to G5 showed generally similar fluorescence intensity and showed not statistically significant difference. The decreased retinal fluorescence intensity means that neovascularization was decreased after the induction of CNV.

From this result, it can be seen that the eye drop of the example of the present disclosure significantly exhibits the effect of decreasing retinal neovascularization not only for the short-term eye drop administration of 2 weeks but also for long-term eye drop administration.

2-2: G2 (EYLEA™) vs G3 (EYLEA™ Administration Interval Doubled+CGK012)

Figure 4A:
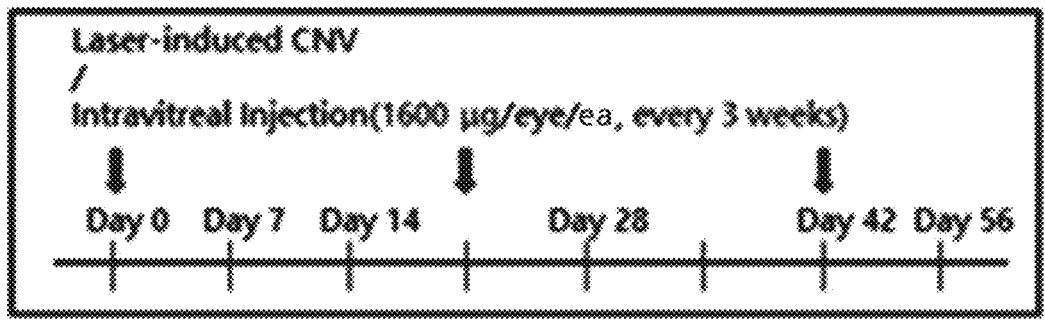
FIG. 4A schematically describes a test method for comparing the retinal fluorescence intensity of an Eylea administration group (G2), which is a positive control group, and an administration group (G3), wherein the administration interval of Eylea was doubled (3 weeks→6 weeks) and CGK012 of an example was co-administered.
Figure 4A:
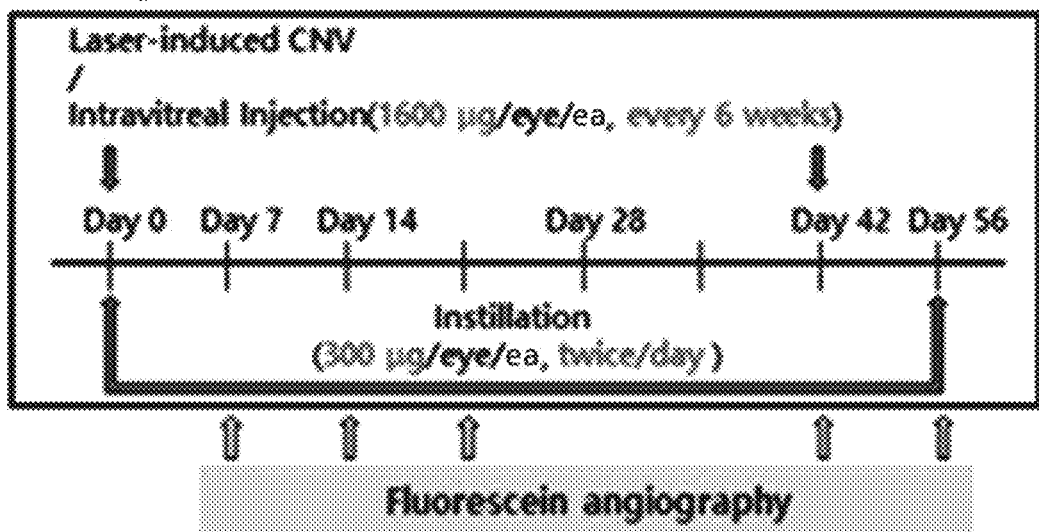
Figure 4B:
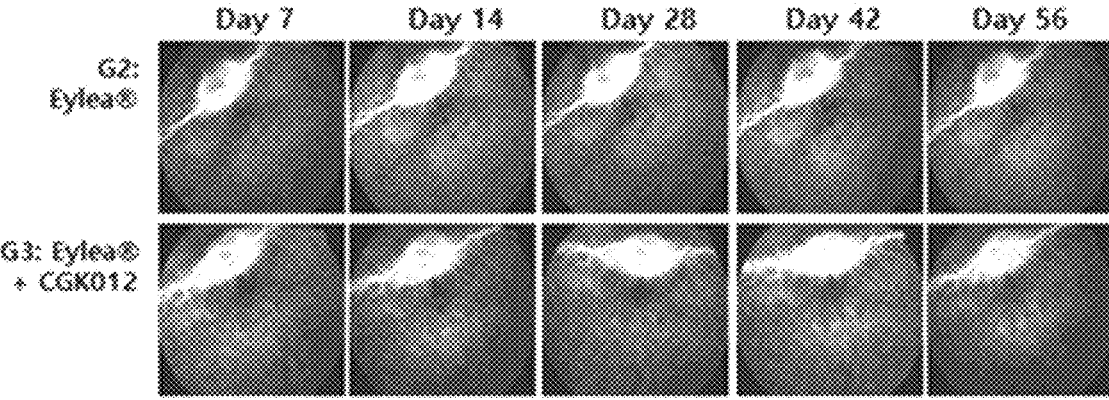
FIG. 4B shows a result of investigating the effect of inhibiting intraocular vascular leakage in a choroidal neovascularization (CNV)-induced mouse model, for the Eylea administration group (G2), which is the positive control group, and the administration group (G3), wherein the administration interval of Eylea was doubled (3 weeks→6 weeks) and CGK012 of the example was co-administered, by fluorescein angiography, and FIG. 4C compares the fluorescence intensity investigated in FIG. 4B with the control group.
Figure 4C:
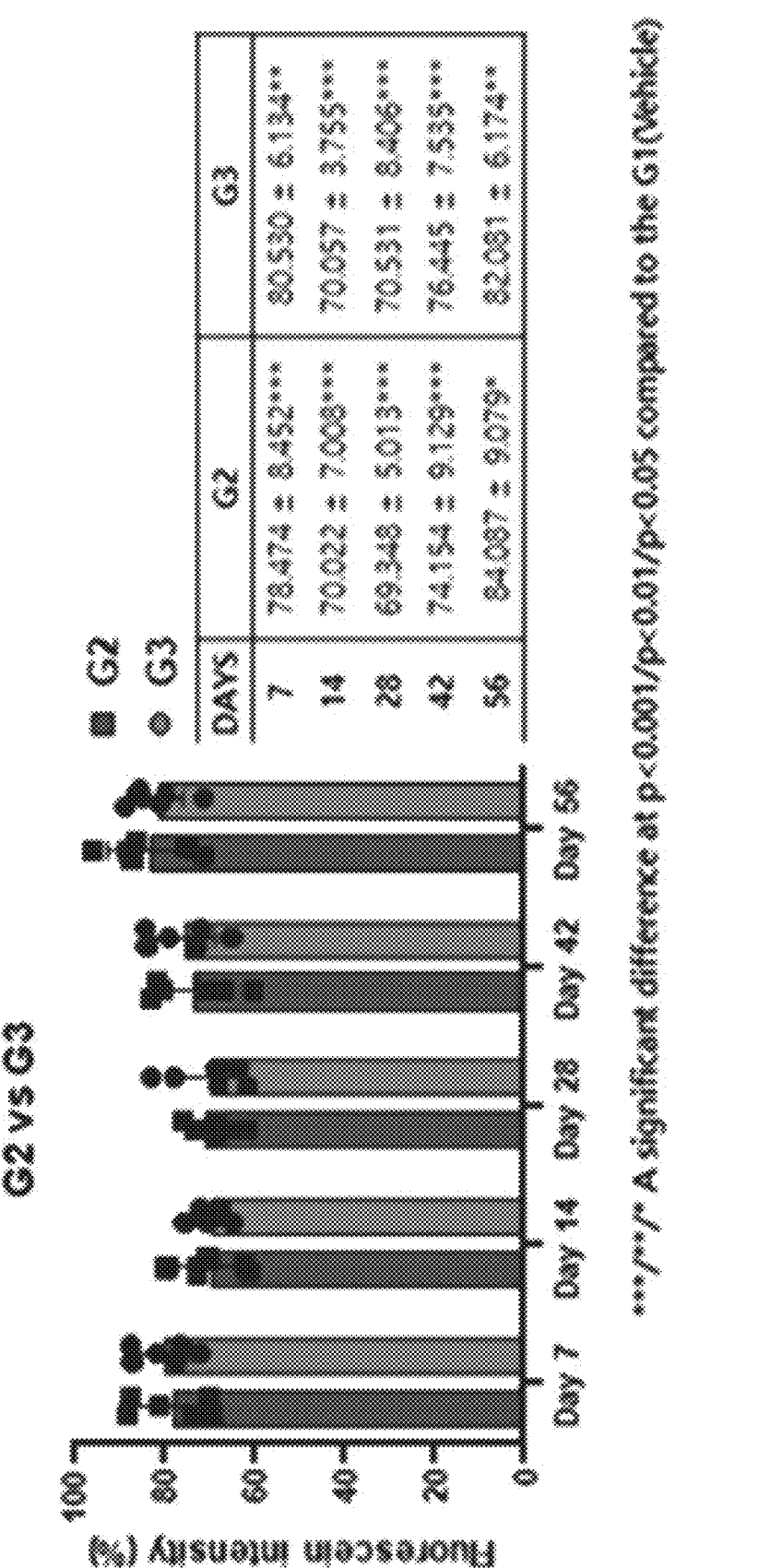

The level of retinal fluorescence intensity was compared for the EYLEA™ administration group (G2), which is a positive control group, and the administration group (G3), wherein the administration interval of EYLEA™ was doubled (3 weeks→6 weeks), and the CGK012 compound of the example was co-administered (FIGS. 4A to 4C).

FIG. 4A schematically describes the test method for comparing the retinal fluorescence intensity of the EYLEA™ administration group (G2), which is a positive control group, and the administration group (G3), wherein the administration interval of EYLEA™ was doubled (3 weeks→6 weeks) and CGK012 of the example was co-administered, FIG. 4B shows the result of investigating the effect of inhibiting intraocular vascular leakage in the chor-oidal neovascularization (CNV)-induced mouse model, for the EYLEA™ administration group (G2), which is the positive control group, and the administration group (G3), wherein the administration interval of EYLEA™ was doubled (3 weeks→6 weeks) and CGK012 of the example was co-administered, by fluorescein angiography, and FIG. 4C compares the fluorescence intensity investigated in FIG. 4B with the control group.

Referring to FIG. 4B and FIG. 4C, the level of retinal fluorescence intensity was significantly low for the administration group (G3), wherein the administration interval of EYLEA™ was doubled (3 weeks→6 weeks) and CGK012 of the example was co-administered, as compared to the induced control group (G1), and showed no statistically significant difference from the positive control EYLEA™ administration group (G2; administration interval=3 weeks).

From this result, it can be seen that the administration interval of the CGK012 compound of the example of the present disclosure can be doubled (3 weeks→6 weeks) as compared to EYLEA™.

2-3: G2 (EYLEA™) vs G4 (EYLEA™ Administration Dosage Halved+CGK012)

Figure 5A:
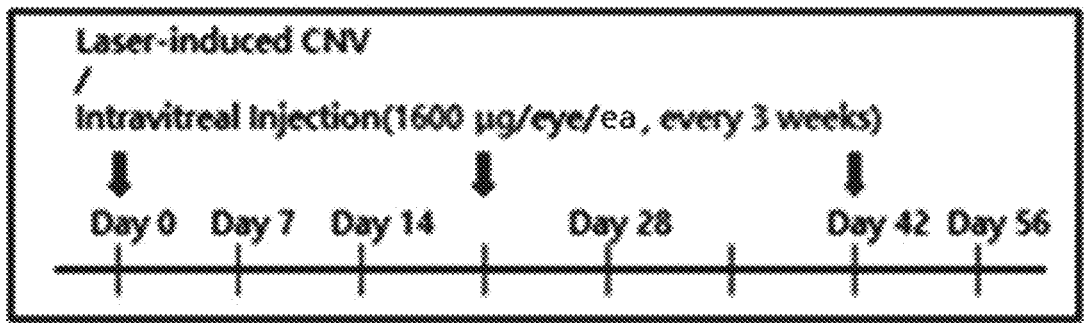
FIG. 5A schematically describes a test method for comparing the retinal fluorescence intensity of an Eylea administration group (G2), which is a positive control group, and an administration group (G4), wherein the administration dosage of Eylea was reduced to ½ (1600 µg→800 µg) and CGK012 of an example was co-administered.
Figure 5A:
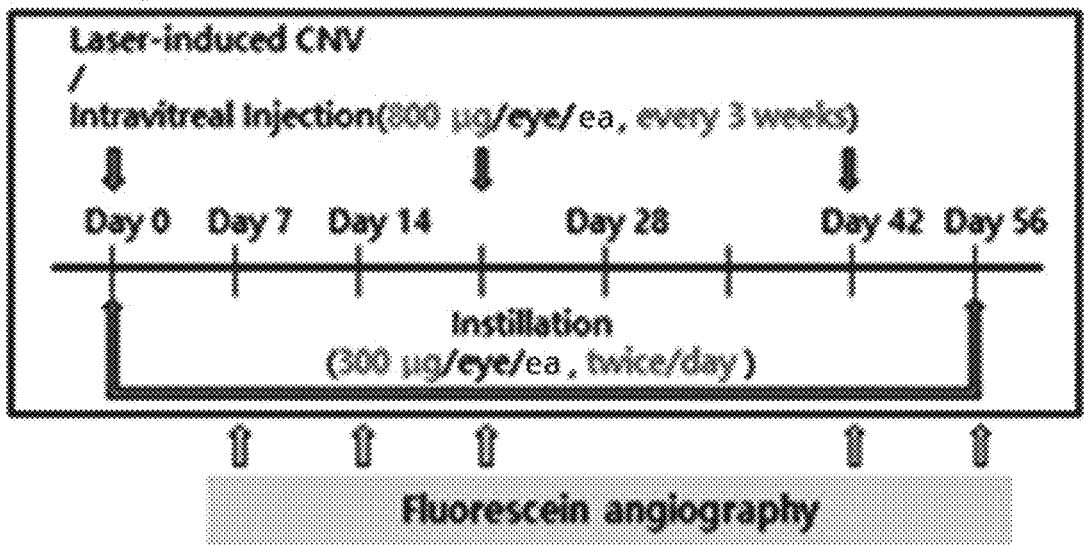
Figure 5B:
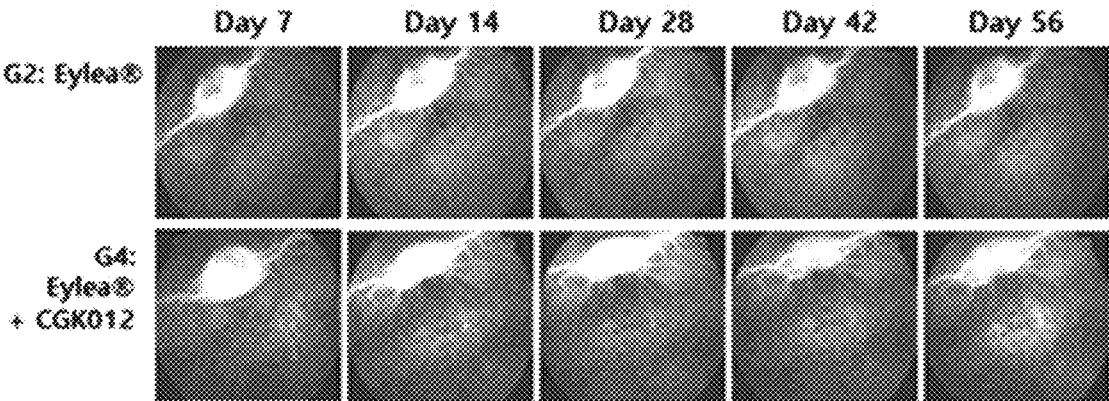
FIG. 5B shows a result of investigating the effect of inhibiting intraocular vascular leakage in a choroidal neovascularization (CNV)-induced mouse model, for the Eylea administration group (G2), which is the positive control group, and the administration group (G4), wherein the administration dosage of Eylea was reduced to ½ (1600 µg→800 µg) and CGK012 of the example was co-administered, by fluorescein angiography, and FIG. 5C compares the fluorescence intensity investigated in FIG. 5B with the control group.
Figure 5C:
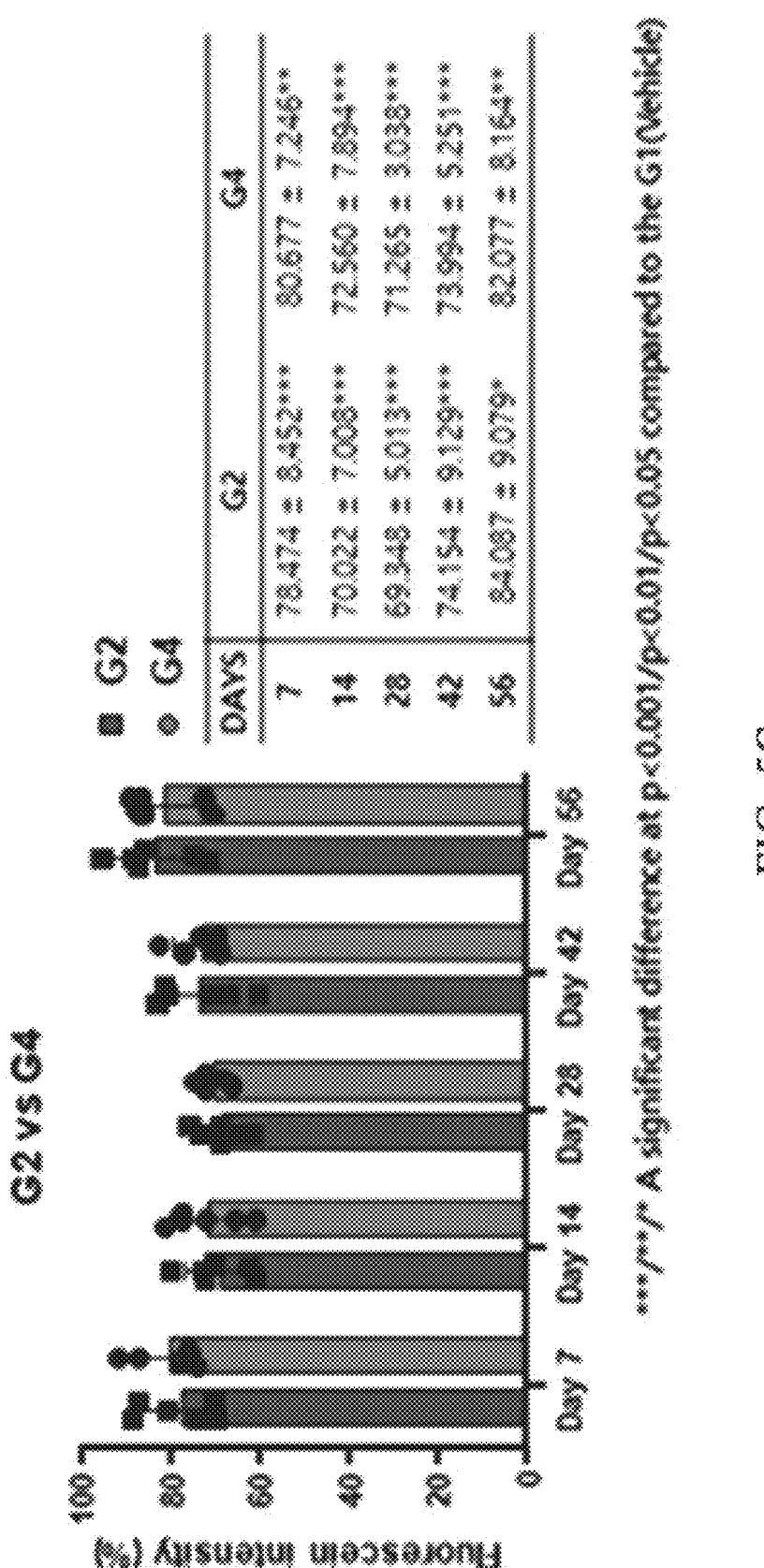

The level of retinal fluorescence intensity was compared for the EYLEA™ administration group (G2), which is a positive control group, and the administration group (G4), wherein the EYLEA™ administration dosage was reduced to ½ (1600 µg→800 µg), and the CGK012 compound of the example was co-administered (FIGS. 5A to 5C).

FIG. 5A schematically describes the test method for comparing the retinal fluorescence intensity of the EYLEA™ administration group (G2), which is a positive control group, and the administration group (G4), wherein the administration dosage of EYLEA™ was reduced to ½ (1600 µg→800 µg) and CGK012 of the example was co-administered, FIG. 5B shows the result of investigating the effect of inhibiting intraocular vascular leakage in the chor-oidal neovascularization (CNV)-induced mouse model, for the EYLEA™ administration group (G2), which is the positive control group, and the administration group (G4), wherein the administration dosage of EYLEA™ was reduced to ½ (1600 µg→800 µg) and CGK012 of the example was co-administered, by fluorescein angiography, and FIG. 5C compares the fluorescence intensity investigated in FIG. 5B with the control group.

Referring to FIG. 5B and FIG. 5C, the level of retinal fluorescence intensity was significantly low for the administration group (G4), wherein the EYLEA™ administration dosage was reduced to ½ (1600 µg→800 µg), and the CGK012 compound of the example was co-administered, as compared to the induced control group (G1), and showed no statistically significant difference from the positive control EYLEA™ administration group (G2; administration dosage=1600 µg).

From this result, it can be seen that the administration dosage of the CGK012 compound of the example of the present disclosure can be reduced to ½ (1600 µg→800 µg) as compared to Eylea.

2-4: G2 (Eylea) vs G5 (CGK012)

Figure 6A:
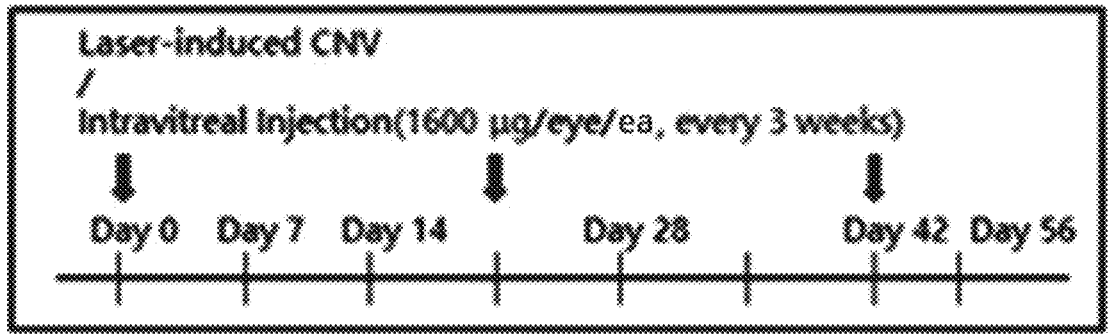
FIG. 6A schematically describes a test method for comparing the retinal fluorescence intensity of an Eylea administration group (G2), which is a positive control group, and an administration group (G5), wherein CGK012 of an example was administered.
Figure 6A:
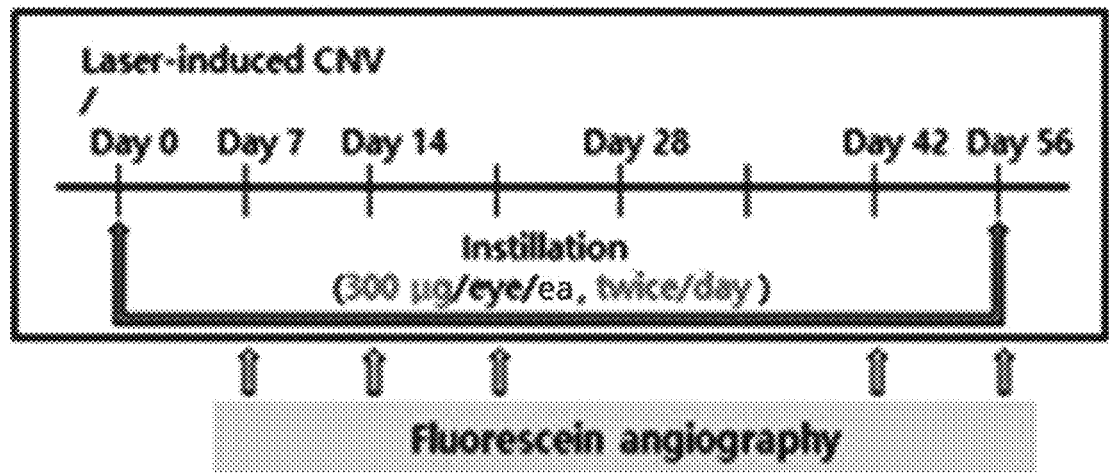
Figure 6B:
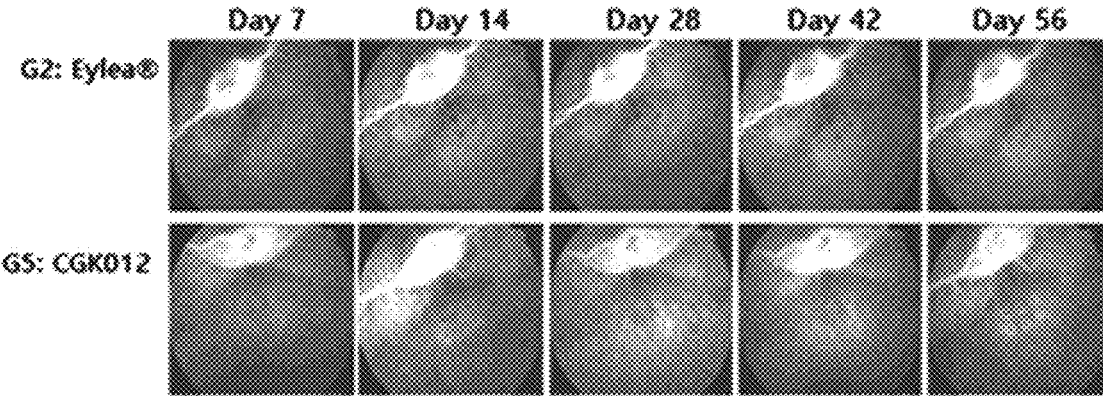
FIG. 6B shows a result of investigating the effect of inhibiting intraocular vascular leakage in a choroidal neovascularization (CNV)-induced mouse model, for the Eylea administration group (G2), which is the positive control group, and the CGK012 administration group (G5), by fluorescein angiography, and FIG. 6C compares the fluorescence intensity investigated in FIG. 6B with the control group.
Figure 6C:
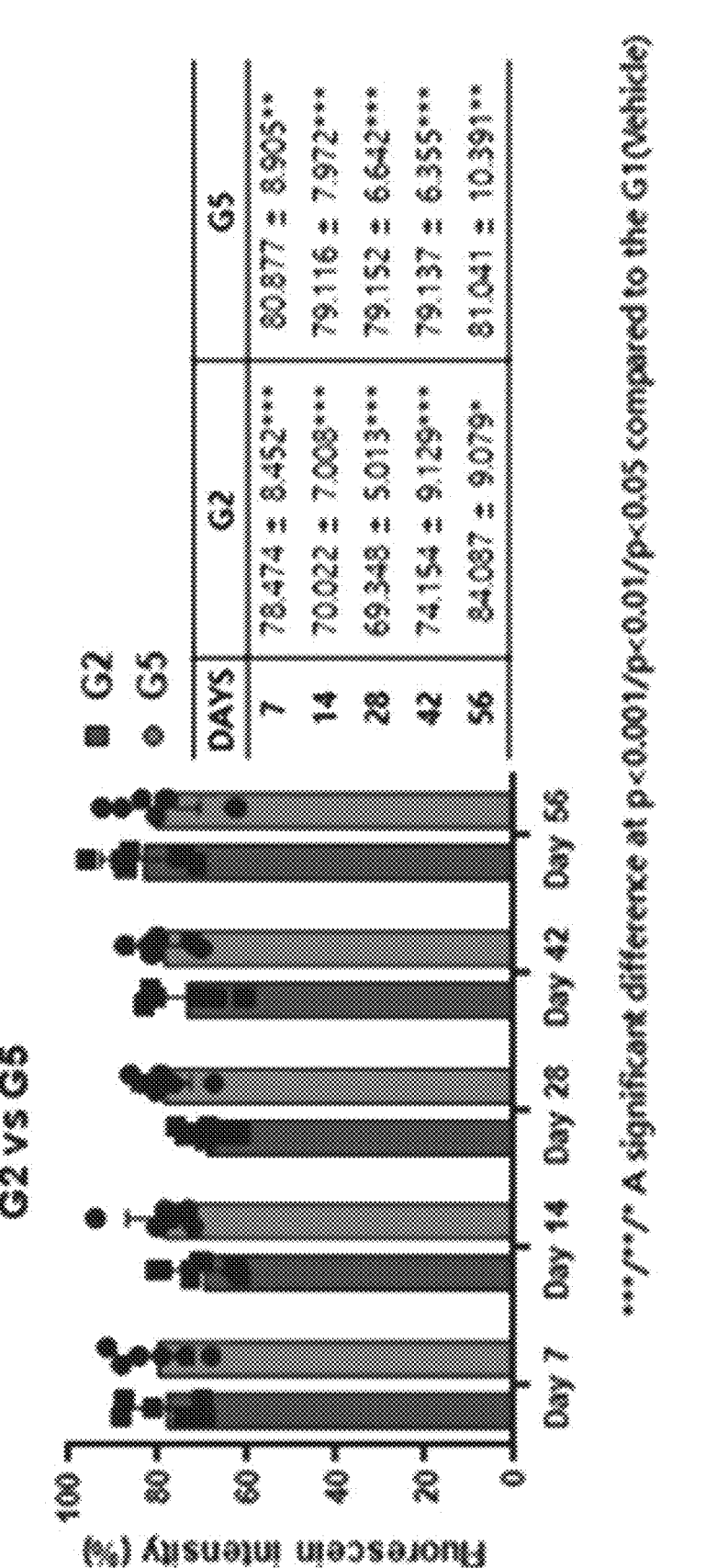

The level of retinal fluorescence intensity was compared for the Eylea administration group (G2), which is a positive control group and the CGK012 administration group (G5) (FIGS. 6A to 6C).

FIG. 6A schematically describes the test method for comparing the retinal fluorescence intensity of the Eylea administration group (G2), which is a positive control group, and the administration group (G5), wherein CGK012 of the example was administered, FIG. 6B shows the result of investigating the effect of inhibiting intraocular vascular leakage in the choroidal neovascularization (CNV)-induced mouse model, for the Eylea administration group (G2), which is the positive control group, and the CGK012 administration group (G5), by fluorescein angiography, and FIG. 6C compares the fluorescence intensity investigated in FIG. 6B with the control group.

Referring to FIG. 6B and FIG. 6C, the level of retinal fluorescence intensity was significantly low for the administration group (G5), wherein the CGK012 compound of the example was administered alone, as compared to the induced control group (G1), and no statistically significant difference was observed from the EYLEA™ administration group (G2), which is the positive control group.

From this result, it can be seen that choroidal neovascularization can be inhibited through single administration of the CGK012 compound of the example of the present disclosure and the effect is continued for 8 weeks. That is to say, it is expected that the CGK012 compound of the example of the present disclosure can replace EYLEA™ which should be administered through intravitreal injection.

To conclude, when the CGK012 compound of the example of the present disclosure was repeatedly adminis-tered to the Chinchilla rabbit CNV model induced with laser irradiation by eye drop administration, the level of retinal fluorescein intensity was maintained at a significantly low level for the CGK012 single administration group, the CGK012+EYLEA™ co-administration group as compared to the CNV induced control group, suggesting that the administration of CGK012 inhibits retinal neovasculariza-tion. Accordingly, it is thought that the repeated eye drop administration of CGK012 in the Chinchilla rabbit CNV model induced with laser irradiation can be helpful in inhibiting choroidal neovascularization.

Test Example 3: Toxicity Test

1) Acute Toxicity

This experiment was conducted to investigate the acute (within 24 hours) toxicity of the compound of the present disclosure and determine its fatality rate when consumed in an excess amount in a short period of time. ICR mice were assigned to a control group (n=5) and a test group (n=5). Nothing was administered to the control group and the compound of Example (1) was orally administered to the test group at a concentration of 2.0 g/kg (about 50 times the amount used in general animal experiments). As a result of examining fatality rate 24 hours after the administration, all the animals of the control group and the test group survived.

2) Organ and Tissue Toxicity of Test Group and Control Group

In order to investigate the effect on the organs (tissues) of C57BL/6J mice, blood was taken from the animals of a test group to which the compound of Example (1) was administered and a control group to which only a solvent was administered 8 weeks after the administration, and blood levels of GPT (glutamate-pyruvate transferase) and BUN (blood urea nitrogen) were measured using SELECT™ E (Vital Scientific NV, Netherlands). As a result, no significant difference was observed in the test group as compared to the control group for GPT, which is known to be related to liver toxicity, and BUN, which is known to be related to kidney toxicity. In addition, the liver and kidney were taken from each animal and subjected to histological observation under an optical microscope through a conventional tissue section preparation process. No unusual abnormality was observed.

Hereinafter, formulation examples containing the (7S)-(+)-cyclopentylcarbarmic acid, 8,8-dimethyl-2-oxo-6,7-di-hydro-2H,8H-pyrano[3,2-g]chromen-7-yl-ester according to the present disclosure as an active ingredient are described. However, they are intended only to specifically describe the present disclosure rather than limiting the same.

Formulation Example 1Preparation of
Pharmaceutical Formulations

Formulation Example 1-1: Preparation of Tablet 20 g of the (7S)-(+)-cyclopentylcarbarmic acid, 8,8-dim-ethyl-2-oxo-6,7-dihydro-2H,8H-pyrano[3,2-g]chromen-7-yl-ester of the present disclosure was mixed with 175.9 g of lactose, 180 g of potato starch and 32 g of colloidal silicic acid. After adding a 10% gelatin solution, the mixture was pulverized and passed through a 14-mesh sieve. After drying and then adding 160 g of potato starch, 50 g of talc and 5 g of magnesium stearate thereto, the mixture was prepared into a tablet.

Formulation Example 1-2: Preparation of Injection 0.5 g of the (7S)-(+)-cyclopentylcarbarmic acid, 8,8-dimethyl-2-oxo-6,7-dihydro-2H,8H-pyrano[3,2-g]chromen-7-yl-ester of the present disclosure was dissolved in distilled water to make 100 mL. The prepared solution was put in a bottle and sterilized by heating for 20-30 minutes.

Formulation Example 2 Preparation of Health
Functional Food

Formulation Example 2-1: Preparation of Dairy Products

After adding 0.1-1.0 wt % of the (7S)-(+)-cyclopentyl-carbarmic acid, 8,8-dimethyl-2-oxo-6,7-dihydro-2H,8H-pyrano[3,2-g]chromen-7-yl-ester of the present disclosure to milk, various dairy products such as butter and ice cream were prepared using the milk.

Formulation Example 2-2: Preparation of Functional Beverage

| Compound prepared in Example (1) | 1,000 mg |
| Citric acid | 1,000 mg |
| Oligosaccharide | 100 g |
| Plum extract | 2 g |
| Taurine | 1 g |
| Purified water | To 900 mL |

After mixing the above ingredients and heating the mixture for about 1 hour while heating at 85° C. under stirring according to a common health beverage preparation method, the prepared solution was filtered into a sterilized 2-L container, sealed and then stored in a refrigerator for use in preparation of a functional beverage composition according to the present disclosure.

Although the above composition is given as a relatively preferred example for a preference beverage, it may be changed arbitrarily according to regional and ethnic preferences such as the consumer class, country, purpose of use, etc.

Although the specific exemplary embodiments of the present disclosure have been described, the present disclosure is not limited thereto but may be modified variously within the scope of the technical idea of the present disclosure and it is obvious that they fall within the scope of the appended claims.

The invention claimed is:

1. A method for treating an eye disease, comprising administering a composition comprising (7S)-(+)-cyclopentylcarbarmic acid, 8,8-dimethyl-2-oxo-6,7-dihydro-2H,8H-pyrano[3,2-g]chromen-7-yl-ester or a pharmaceutically acceptable salt thereof to a subject in need thereof.

2. The method according to claim 1, wherein the eye disease is one or more disease selected from ocular neovascularization, macular degeneration, maculopathy, macular edema, retinal degeneration, retinal edema, retinopathy, macula tumentia and glaucoma.

3. The method according to claim 2, wherein the macular degeneration is age-related macular degeneration (AMD).

4. The method according to claim 1, wherein the composition is a composition for topical administration to the eye.

5. The method according to claim 4, wherein the composition for topical administration to the eye is formulated as an eye drop, an ointment or an ophthalmic injection.

6. The method according to claim 1, wherein the composition inhibits intraocular vascular leakage.

7. The method according to claim 1, wherein the composition further comprises one or more pharmaceutically acceptable carrier, excipient, or diluent.

8. The method according to claim 1, wherein the composition is administered parenterally.

9. The method according to claim 8, wherein the parenteral administration is selected from the group consisting of intraocular injection, intravitreal injection, subretinal injection, suprachoroidal injection, eye drop administration, and any combination thereof.

* * * * *